United States Patent [19]

Hindley

[11] 4,271,188
[45] Jun. 2, 1981

[54] COMPOUNDS HAVING HYPOLIPIDAEMIC ACTIVITY

[75] Inventor: Richard M. Hindley, Reigate, England

[73] Assignee: Beecham Group Limited, England

[21] Appl. No.: 104,418

[22] Filed: Dec. 17, 1979

Related U.S. Application Data

[63] Continuation of Ser. No. 870,462, Jan. 18, 1978, abandoned.

[30] Foreign Application Priority Data

Jan. 22, 1977 [GB] United Kingdom ............... 2659/77

[51] Int. Cl.³ ............... A61K 31/245; A61K 31/24; C07C 101/447; C07C 101/60
[52] U.S. Cl. ................................. 424/309; 424/279; 424/301; 424/310; 424/316; 424/318; 424/319; 424/324; 260/343.3 R; 260/404; 260/463; 260/501.1; 560/21; 560/27; 560/28; 560/45; 560/47; 560/48; 562/452; 562/455; 562/456; 562/457; 564/163; 564/166; 564/167

[58] Field of Search ............... 560/47, 48, 45; 424/309, 310, 318, 316, 319, 279, 301; 260/404, 343.3 R, 463; 562/452, 456, 457, 455

[56] References Cited

U.S. PATENT DOCUMENTS 3,957,850  5/1976  Bouchara ........................... 560/47

FOREIGN PATENT DOCUMENTS 2609962  9/1976  Fed. Rep. of Germany ............ 560/48
2193579  2/1974  France ............................. 560/47

OTHER PUBLICATIONS

Hayes et al., J. Chem. Soc., 1088, 1970.
West, Chem. Absts., 40, 559(3), 1946.
Mondon, Chem. Absts., 54, 13154(g), 1960.

Primary Examiner—G. T. Breitenstein
Attorney, Agent, or Firm—Jacobs & Jacobs

[57] ABSTRACT

Compounds having hypolipidaemic activity which are substituted aralkylanilines, their preparation and pharmaceutical compositions containing them.

20 Claims, No Drawings

COMPOUNDS HAVING HYPOLIPIDAEMIC ACTIVITY

This is a continuation of Ser. No. 870,462, filed Jan. 18, 1978, now abandoned.

This invention relates to compounds which have hypolipidaemic activity and in particular to a class of substituted aralkylanilines to a method for their preparation and to pharmaceutical compositions containing them.

In our U.K. application No. 5287/76 we have disclosed a class of aralkylanilines of formula (I) as having hypolipidaemic acticity:

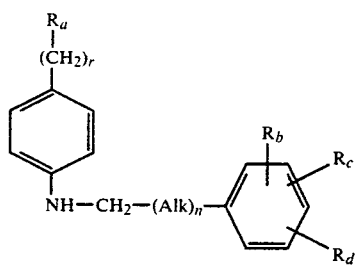

(I)

wherein $R_a$ is a carboxylic acid group or a pharmaceutically acceptable salt or ester of a carboxylic acid group; an alkyl group optionally substituted by one or more hydroxyl groups; or a cyano, or acyl group:

r is zero or an integer from 1–12

Alk represents a straight or branched chain alkylene group;

n is zero or one;

$R_b$ and $R_c$ are the same or different and each is hydrogen, halogen, $C_{1-8}$ alkyl, $C_{1-8}$ alkoxy;

$R_d$ is hydrogen, halogen, $C_{1-8}$ alkoxy, halo($C_{1-8}$) alkyl, nitro, carboxylic acid or a salt or ester thereof, hydroxy, amino, alkylamino, acylamino, phenyl; or any two groups $R_b$, $R_c$, $R_d$, on adjacent carbon atoms form the residue of a fused benzene ring.

We have now found that a series of N-substituted aralkylanilines also have useful hypolipidaemic activity.

Accordingly, the present invention provides a compound of formula (II):

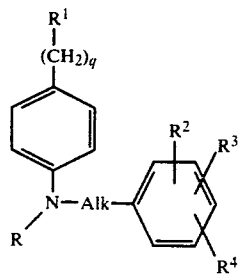

(II)

wherein $R^1$ represents a carboxylic acid group or a pharmaceutically acceptable salt or ester of a carboxylic acid group; or an alkyl, hydroxyalkyl, alkanoylalkyl, hydroxyalkanoyl or an optionally salted or esterified carboxyalkanoyl group;

q is zero or an integer from 1–12;

Alk represents a straight or branched chain alkylene group;

$R^2$ and $R^3$ are the same or different and each is hydrogen, halogen, $C_{1-8}$ alkyl, $C_{1-8}$ alkoxy;

$R^4$ is hydrogen, halogen $C_{1-8}$ alkoxy; halo($C_{1-8}$) alkyl, nitro, carboxylic acid or a salt or ester thereof, hydroxy, amino, alkylamino, acylamino; or any two groups $R^2$, $R^3$, $R^4$, on adjacent carbon atoms form the residue of a fused benzene ring;

R is a carboxylic ester group, a formyl, alkanoyl $C_{1-12}$ alkyl group or a substituted carbamyl group of formula $CO.NR^xR^y$ in which $R^x$ and $R^y$ are each a $C_{1-6}$ alkyl group or together form a $C_5$–$C_6$ alkylene moiety.

Suitable ester groups for R and $R^1$ include an alkyl, cycloalkyl, alkenyl, alkynyl, aryl aralkyl or heterocyclic group or a group known to readily hydrolyse in the human body to produce the parent acid. Suitable examples include acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl.

Preferred ester groups for R and $R^1$ are $C_{1-6}$ alkyl ester groups, particularly methyl and ethyl esters.

The alkyl group within the definition of R or $R^1$ may suitably have from 1–10 carbon atoms preferably from 1–6 carbon atoms, such as methyl, ethyl, straight or branched chain propyl, butyl, pentyl, hexyl; and may be substituted at any position with one or more hydroxy groups.

Suitable alkanoyl groups within the definitions R and $R^1$ include alkanoyl groups having from 2–7 carbon atoms, especially acetyl, propionyl and butyryl.

Suitable examples of the group $R^1$ include the following: carboxylic acid, —$CO_2H$ or a salt, especially when q is zero or 2;

methoxycarbonyl, $CO_2CH_3$;

ethoxycarbonyl, $CO_2C_2H_5$;

methyl;

hydroxymethyl, —$CH_2OH$;

acetylmethyl, —$CH_2COCH_3$;

hydroxyacetyl, —$COCH_2OH$;

hydroxypropionyl, —$COCH_2CH_2OH$;

carboxyacetyl, —$COCH_2CO_2H$;

methoxycarbonylacetyl, —$COCH_2CO_2CH_3$;

ethoxycarbonylacetyl, —$COCH_2CH_2COCH_3$;

Suitably q may equal zero or an integer from 1–6, particularly 1–2.

The group 'Alk' may suitably be a $C_{1-10}$ alkylene chain more suitably $C_{1-6}$ alkylene such as methylene, ethylene, propylene, butylene. Preferably 'Alk' represents methylene.

Suitable groups $R^2$ and $R^3$ include hydrogen, chlorine, bromine, fluorine, methyl, ethyl, n- and iso-propyl n-, iso-, sec- and t-butyl, pentyl, hexyl, methoxy, ethoxy, n- and iso propoxy, n- iso, sec-, and t-butoxy, pentyloxy, hexyloxy.

Suitably one of the groups $R^2$ and $R^3$ is hydrogen.

Preferably both $R^2$ and $R^3$ are hydrogen, and $R^4$ is a halogen atom, especially a 4-chloro substituent.

Thus one important sub-class of compounds within the present invention is represented by formula (III):

(III)

$$\text{Structure: 4-CO}_2\text{R}^5\text{-C}_6\text{H}_4\text{-N(R}^7\text{)-CH}_2\text{-C}_6\text{H}_4\text{-R}^6$$

wherein $R^5$ is hydrogen, a salting ion or a $C_{1-6}$ alkyl group, $R^6$ is halogen, preferably chlorine, and $R^7$ is a formyl, $C_{1-6}$ alkanoyl, $C_{1-6}$ alkyl or $C_{1-6}$ alkoxycarbonyl group.

Specific compounds of this invention include:

N-(4-ethoxycarbonylphenyl)-N-(4-chlorobenzyl)-formamide;

ethyl N-(4-ethoxycarbonylphenyl)-N-(4-chlorobenzyl)-carbamate;

ethyl N-(4-methoxycarbonylphenyl)-N-(4-fluorobenzyl)-carbamate;

N-(4-ethoxycarbonylphenyl)-N-(4-chlorobenzyl)-methylamine;

N-(4-ethoxycarbonylphenyl)-N-(4-chlorobenzyl)-acetamide;

N-(4-ethoxycarbonylphenyl)-N-(4-chlorobenzyl)-ethylamine;

N-(4-ethoxycarbonylphenyl)-N-(4-chlorobenzyl)-propylamine;

N-(4-ethoxycarbonylphenyl)-N-(4-chlorobenzyl)-heptylamine;

N-(4-ethoxycarbonylphenyl)-N-(4-fluorobenzyl)-hexylamine;

N-(4-ethoxycarbonylphenyl)-N-(4-chlorobenzyl)-butylamine;

N-(4-ethoxycarbonylphenyl)-N-(4-ethoxycarbonylphenyl)-N-(4-chlorobenzyl)-decylamine;

N-(4-acetonylphenyl)-N-(4-chlorobenzyl)-methylamine;

N-[4-(2-ethoxycarbonylethyl)-phenyl]-N-(4-chlorobenzyl)-methylamine;

The compounds of this invention may be prepared by reacting a compound of formula (IV) with a compound of formula (V):

$$\underset{(IV)}{A-\underset{H}{N}-B} \qquad \underset{(V)}{D-X}$$

wherein X represents a reactive group; one group A, B or D represents a group of formula (VI):

(VI)

$$\text{4-R}^1\text{-(CH}_2)_q\text{-C}_6\text{H}_4\text{-}$$

(wherein $R^1$ and q are as defined above with respect to formula (I)); one group A, B or D represents a group of formula (VII):

(VII)

$$\text{-Alk-C}_6\text{H}_2(\text{R}^2)(\text{R}^3)(\text{R}^4)$$

(wherein Alk, $R^2$, $R^3$ and $R^4$ are as defined above with respect to formula (I)); and the third group A, B or D represents the group R as defined with respect to formula (I); and optionally converting one group $R^1$ into another group $R^1$.

The reactive group is such that when compound (V) is reacted with compound (IV), the elements of a compound H-X are eliminated and the group D becomes attached to the nitrogen atom of compound (IV).

Preferably the groups A and B represent groups (VI) and (VII) and the group D represents R.

The nature of the group X then depends on the nature of the group R to which it is attached. For example the reactive group X may be a halogen atom, especially chlorine or bromine when R is a carboxylic ester group, an acyl group, an alkyl group or a group $CO.NR^xR^y$; or X may be an acyloxy group especially acetoxy, propionoxy, when R is an acyl group. Alternatively, X may be alkyl- or aryl- sulphonyloxy, such as methanesulphonyloxy, benzenesulphonyloxy, p-toluenesulphonyloxy, when R is an alkyl group.

The intermediates of formula (IV) in which A and B represent groups (VI) and (VII) may be prepared as described in U.K. patent application No. 5287/76.

The reaction may also be conveniently carried out when A represents the group of formula (VI), B represents R, and D represents group (VII).

The reaction is less satisfactory in the case when A represents group (VII), B represents R and D represents group (VI).

After the above reaction, the group $R^1$ may be converted into a different group $R^1$.

Alternative methods of preparing compounds wherein $R^1$ represents an ester group include the esterification of the free acid or its salt or other reactive derivative of the acid, or transesterification of a compound having a different ester group. Esterification may be performed by any conventional method, for example by reaction of the free acid with the appropriate alcohol in the presence of a catalyst such as a strong acid, dry hydrogen chloride, or p-toluenesulphonic acid.

The formation of compounds (II) wherein $R^1$ is an ester may also be carried out by conventional transesterification methods, for example reaction of an ester with the appropriate second alcohol in the presence of a catalyst such as the sodium salt of the alcohol, or dry hydrogen chloride, p-toluenesulphonic acid or potassium cyanide.

Compounds of formula (II) wherein $R^1$ is an ester may also be prepared by alkanolysis of the corresponding cyano compound ($R^1$ is C≡N); or by hydrolysis of an iminoether compound having formula (II) wherein $R^1$ is a group of formula:

$$R^ZO-\underset{NH}{\overset{\|}{C}}-$$

wherein $R^Z$ is the hydrocarbon residue of an alcohol or phenol.

Compounds wherein $R^1$ represents a carboxylic acid group can also be prepared by the acid or base catalysed hydrolysis of the corresponding compound of formula (II) wherein $R^1$ is selected from:
(a) carboxylic acid amide group;
(b) esterified carboxylic acid group.

Hydrolysis of amides may be carried out using a mineral acid as catalyst, suitably hydrochloric acid or sulphuric acid. Base catalysed hydrolysis may be carried out using an alkali metal or alkaline earth metal hydroxide, e.g. sodium or potassium hydroxide. Suitably, the hydrolysis reaction is carried out in aqueous solution e.g. refluxing for several hours. The desired compound can be isolated as the free acid by neutralisation of the resultant reaction mixture or as the appropriate base addition salt (e.g. sodium salt if sodium hydroxide was employed) or acid addition salt (e.g. the hydrochloride if HCl was employed). Alternatively, the free acid can be converted to any desired salt by standard procedures.

For the hydrolysis of an esterified carboxylic acid group, preferably the process involves hydrolysis with a strong base such as sodium hydroxide. The esterified carboxylic acid groups $R_1$ may be, for example lower alkoxycarbonyl groups such as methoxycarbonyl or tertiary butoxycarbonyl groups. The remarks made earlier about salts of the resultant free acid also apply in this case.

A further method for the preparation of compounds of formula (II) in which R represents an alkyl group having two or more carbon atoms is the reduction of a compound of formula (II) in which R represents an alkanoyl group. A suitable reagent for this process is borane in dimethyl sulphide.

This invention also provides a pharmaceutical composition which comprises at least one compound of formula (II) as hereinbefore defined together with at least one pharmaceutically acceptable carrier.

The composition may be formulated for administration by any route, although oral administration is preferred. The compositions may be in the form of tablets, capsules, powders, granules, lozenges, or liquid preparations such as oral sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium, phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain additives such as suspending agents, for example, sorbitol, methyl sellulose, glucose syrup, gelatin, hydroxyethylcellulose, carboxymethyl cellulose, aluminium stearate gel or hydrogenated edible fats, emulsifying agents, for example lecithin, sorbital monooleate, or acacia, non-aqueous vehicles (which may include edible oils) for example almond oil, fractionated coconut oil, oily esters such as glycerine, propylene gycol, or ethyl alcohol; preservatives, for example methyl or propyl p-hydroxybenzoate or sorbic acid, and if desired convention flavouring or colouring agents.

Suppositories will contain conventional suppository bases, e.g. cocoa butter or other glyceride.

For parenteral administration, fluid unit dosage forms are prepared utilizing the compounds and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as local anesthetic, preservative and buffering agents can be dissolved in the vehicle. To enhance the stability, the composition can be frozen after filling into the vial and the water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The composition may contain from 0.1% or 99% by weight, preferably from 10–60% by weight, of the active material, depending on the method of administration. Where the compositions comprise dosage units, each unit will preferably contain from 250 mg–3 g of the active ingredient. The dosage as employed for adult human treatment will preferably range from 1 to 10 g., per day, for instance 3 g, per day, depending on the route and frequency of administration.

Also included within the scope of the present invention is a method for controlling or reducing the serum lipid levels of mammals, including man which method comprises the administration to the mammal of one or more of the compounds of formula (II) above. An oral administration is preferred.

The compound may be administered alone in combination with one or more pharmaceutically acceptable carriers, or as part of the total dietary intake. In the latter case, the amount of said compound employed may be less than 1% by weight of the diet and is preferably no more than 0.5% by weight. The diet for a man may consist of normal food stuffs to which the ester has been added, and similarly the diet for animals may consist of foodstuffs and the compound may be added alone or with a premix.

The following Examples illustrate this invention.

EXAMPLE 1

Preparation of N-(4-ethoxycarbonylphenyl)-N-(4-chlorobenzyl-formamide

Ethyl 4-(4-chlorobenzylamino)-benzoate (7.2 g; 0.025 mole) was dissolved in formic acid (80%; 70 ml) and the solution was heated to 55° C. with stirring. Acetic anhydride (25 ml) was added dropwise at this temperature, allowed to cool to room temperature and stirred for 1 hour. The reaction mixture was added to iced water (100 ml) and the aqueous mixture was neutralised with solid sodium bicarbonate. The product was extracted into dichloromethane (2×100 ml), washed with water (1×100 ml), dried (anhydrous MgSO₄) and evaporated. Pure N-(4-ethoxycarbonylphenyl)-N-(4-chlorobenzyl)-formamide (5.32 g; 67%) was obtained by chromatography on silica-gel in dichloromethane followed by crystallisation from ethanol. M.p. 72°-3° C.

|   | Analysis Required | Found |
|---|---|---|
| C | 64.25 | 63.95 |
| H | 5.04 | 5.18 |
| N | 4.41 | 4.30 |
| Cl | 11.18 | 11.22 |

EXAMPLE 2

Preparation of Ethyl N-(4-ethoxycarbonylphenyl)-N-(4-chlorobenzyl)-carbamate

A stirred solution of ethyl 4-(4-chlorobenzylamino)-benzoate (5.8 g; 0.02 mole) in pyridine (50 ml) was treated dropwise with ethyl chloroformate (2.5 g; 0.023 mole) at room temperature. The mixture was heated to 100° C. for 30 minutes, cooled and added to iced water (100 ml). After neutralisation with dilute hydrochloric acid the product was extracted into dichloromethane (2×100 ml), washed with water (1×100 ml), dried (anhydrous MgSO₄) and the solvent evaporated. The residual oil was purified by chromatography on silica-gel in dichloromethane to give ethyl N-(4-ethoxycarbonylphenyl)-N-(4-chlorobenzyl)-carbamate as a colourless oil (4.86 g; 56%) which solidifed on standing. M.p. 43°-6° C.

|   | Analysis Required | Found |
|---|---|---|
| C | 63.07 | 63.19 |
| H | 5.57 | 5.92 |
| N | 3.87 | 3.95 |
| Cl | 9.82 | 10.82 |

EXAMPLE 3

Ethyl N-(4-methoxycarbonylphenyl)-N-(4fluorobenzyl)-carbamate

This compound was prepared by the method of Example 2 using methyl 4-(4-fluorobenzylamino)-benzoate in place of ethyl 4-(4-chlorobenzylamino)-benzoate. The product had m.p. 83°-4° C.

EXAMPLE 4

Preparation of N-(4-ethoxycarbonylphenyl)-N-(4-chlorobenzyl)-methylamine

To ethyl-4-(4-chlorobenzylamino)-benzoate (5.8 g; 0.02 mole) was added 80% formic acid (30 ml) and 40% formaldehyde solution (10 ml) and the mixture was heated at 100° C. for 6 hours. The reaction mixture was cooled to room temperature, water (60 ml) added and the product filtered, dried under vacuum at 60° C. and was crystallised from ethanol to give N-(4-ethoxycarbonylphenyl)-N-(4-chlorobenzyl)-methylamine (4.86 g; 80%). M.p. 106°-7° C.

|   | Analysis Required | Found |
|---|---|---|
| C | 67.21 | 66.96 |
| H | 5.93 | 5.99 |
| N | 4.61 | 4.55 |
| Cl | 11.70 | 11.89 |

EXAMPLE 5

Preparation of N-(4-ethoxycarbonylphenyl)-N-(4-chlorobenzyl)-acetamide

Ethyl 4-(4-chlorobenzylamino)-benzoate (11.56 g; 0.04 M), acetic anhydride (40 ml) and concentrated sulphuric acid (5 drops) were mixed and heated with stirring on a steam-bath for 1 hour. The mixture was cooled to room temperature, added to iced water (100 ml) and neutralised with solid sodium bicarbonate. The product was extracted into dichloromethane (2×100 ml), washed with water (1×100 ml) and evaporated to give an oil from which N-(4-ethoxycarbonylphenyl)-N-(4-chlorobenzyl)-acetamide (8.32 g; 63%) was obtained by chromatography on silica-gel in dichloromethane then 2% methanol-dichloromethane followed by crystallisation from ethanol. M.p. 65°-6° C.

|   | Analysis Required | Found |
|---|---|---|
| C | 65.16 | 65.27 |
| H | 5.43 | 5.38 |
| N | 4.22 | 4.22 |
| Cl | 10.71 | 10.20 |

EXAMPLE 6

Preparation of N-(4-ethoxycarbonylphenyl)-N-(4-chlorobenzyl)-ethylamine

To a solution of ethyl 4-(4-chlorobenzylamino)-benzoate (29.0 g; 0.10 M) in dry dimethylformamide (300 ml) under nitrogen was added sodium hydride (2.64 g; 0.11 M) with stirring. The mixture was stirred at 70° C. for 4 hours and then at room temperature for 16 hours. Ethyl iodide (31.2 g; 0.2 M) was added dropwise to the stirred solution over a period of 45 minutes and the mixture was heated at 60° C. for 1.5 hours. The solution was cooled to room temperature, poured onto iced water (800 ml) and the product extracted into ether (2×500 ml). The organic extracts were washed with water (2×700 ml), dried (MgSO₄) and the solvent removed under reduced pressure to give 31 g of yellow oil.

Chromatography on silica-gel (1 Kg) in dichloromethane and crystallisation of product from IPA gave N-(4-ethoxycarbonyl-phenyl)-N-(4chlorobenzyl)-ethylamine (15.5 g; 49%). M.p. 48°-50° C.

|   | Analysis Required | Found |
|---|---|---|
| C | 68.02 | 67.95 |
| H | 6.34 | 6.30 |
| N | 4.41 | 4.37 |
| Cl | 11.16 | 11.18 |

EXAMPLES 7-8

The following compounds were prepared by the method of Example 6:

EXAMPLE 7

Preparation of
N-(4-ethoxycarbonylphenyl)-N-(4-chlorobenzyl)-propylamine

B.p. 228°-234° C. (0.7 mm)

|   | Analysis | |
|---|---|---|
|   | Required | Found |
| C | 68.77 | 68.59 |
| H | 6.66 | 6.64 |
| N | 4.22 | 4.04 |

EXAMPLE 8

Preparation of
N-(4-ethoxycarbonylphenyl)-N-(4-chlorobenzyl)-heptylamine

M.p. 67°-69° C.

|   | Analysis | |
|---|---|---|
|   | Required | Found |
| C | 71.21 | 70.91 |
| H | 7.80 | 7.77 |
| N | 3.61 | 3.55 |
| Cl | 9.14 | 9.34 |

EXAMPLE 9

Preparation of
N-(4-ethoxycarbonylphenyl)-N-(4-fluorobenzyl)-hexylamine

Ethyl 4-(N-hexylamine)-benzoate (4.98 g; 0.02 M) was dissolved in a mixture of potassium carbonate (2.76 g; 0.02 M) in hexemethylphosphoramide (30 ml). 4-fluorobenzyl chloride (2.90 g; 0.02 M) was added and the mixture was heated at 120° C. with stirring for 36 hours. The reaction mixture was cooled, added to iced water (100 ml) and extracted with dichloromethane (2×100 ml). The organic extracts were dried (MgSO$_4$) and the solvent removed under reduced pressure to give 16.8 g of green oil.

Chromatography on silica gel (500 g) in dichloromethane and crystallisation from ethanol gave N-(4-ethoxycarbonylphenyl)-N-(4-fluorobenzyl)-hexylamine (1.57 g; 22%). M.p. 41°-2° C.

|   | Analysis | |
|---|---|---|
|   | Required | Found |
| C | 73.95 | 73.91 |
| H | 7.84 | 7.62 |
| N | 3.92 | 3.80 |

BIOLOGICAL DATA

The hypocholesterolaemic and/or hypotriglyceridaemic effects of several compounds of the present invention were demonstrated in the following experiment: Groups of 8 male albino rats (C.F.Y. strain), weighing approximately 150 g, were given a powdered commercially available diet (oxoid) to which compounds were added at level of 0.25%. These diets were fed for seven days. The rats were then killed and their serum total cholesterol and triglyceride were measured by the Technicon Autoanalyser.

Table 1 shows the results expressed in terms of percentage cholesterol lowering and percentage triglyceride lowering compared with controls.

TABLE I

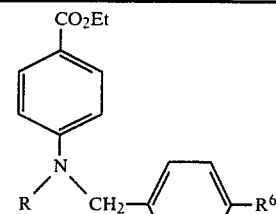

| Example No. | R | $R^6$ | % Cholesterol Lowering | % Triglyceride Lowering |
|---|---|---|---|---|
| 1 | —CHO | —Cl | 22 | 79 |
| 2 | —CO$_2$Et | —Cl | 33 | 72 |
| 3 | —CO$_2$Et | —F | 33 | 23 |
| 4 | —CH$_3$ | —Cl | 27 | 74 |
| 5 | —COCH$_3$ | —Cl | 10 | 31 |
| 6 | —CH$_2$CH$_3$ | —Cl | 52 | 47 |

What we claim is:

1. A compound of formula (II):

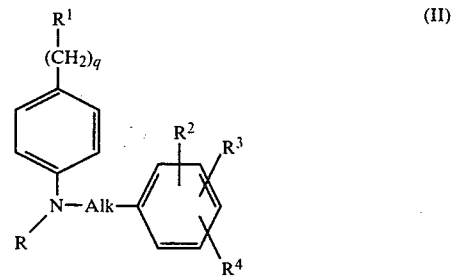

wherein $R^1$ represents carboxylic acid or a salt or ester thereof;

q is zero or an integer from 1 to 12;

Alk represents straight or branched chain alkylene;

$R^2$ and $R^3$ are the same or different and each is hydrogen, halogen, $C_{1-8}$ alkyl, $C_{1-8}$ alkoxy;

$R^4$ is hydrogen, halogen, $C_{1-8}$ alkoxy, hydroxy or acylamino, or any two of groups $R^2$, $R^3$, $R^4$ represent a fused benzene ring; and R is methyl.

2. A compound as claimed in claim 1 wherein $R^1$ is carboxylic acid or a pharmaceutically acceptable salt or $C_{1-6}$ alkyl ester thereof.

3. A compound as claimed in claim 1 wherein $R^1$ represents carboxy, methoxycarbonyl or ethoxycarbonyl.

4. A compound as claimed in claim 1 wherein q is zero or an integer from 1 to 6.

5. A compound as claimed in claim 1 in which 'alk' represents an alkylene chain having from 1 to 6 carbon atoms.

6. A compound as claimed in claim 1 wherein $R^2$ and $R^3$ are hydrogen.

7. A compound as claimed in claim 1 wherein $R^4$ is a halogen atom.

8. A compound as claimed in claim 1 having the formula (III):

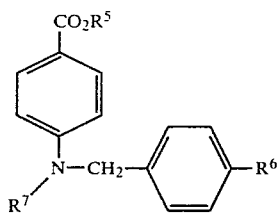

wherein $R^5$ is hydrogen, a salting ion or a $C_{1-6}$ alkyl group, $R^6$ is halogen, and $R^7$ is methyl.

9. N-(4-Ethoxycarbonylphenyl)-N-(4-chlorobenzyl)-methylamine.

10. N-(4-Ethoxycarbonylphenyl)-N-(4-chlorobenzyl)-ethylamine.

11. N-(4-Ethoxycarbonylphenyl)-N-(4-chlorobenzyl)-propylamine.

12. N-(4-Ethoxycarbonylphenyl)-N-(4-chlorobenzyl)-heptylamine.

13. N-(4-Ethoxycarbonylphenyl)-N-(4-fluorobenzyl)-hexylamine.

14. N-(4-Ethoxycarbonylphenyl)-N-(4-chlorobenzyl)-butylamine.

15. N-(4-Ethoxycarbonylphenyl)-N-(4-chlorobenzyl)-decylamine.

16. N-[4-(2-Ethoxycarbonylethyl)-phenyl]-N-(4-chlorobenzyl)-methylamine.

17. A pharmaceutical composition for the treatment or control of hyperlipidaemia comprising a pharmaceutically acceptable carrier together with a hypolipidaemically effective amount of a compound as claimed in claim 1.

18. A pharmaceutical composition for the treatment or control of hypolipidaemia comprising a pharmaceutically acceptable carrier together with a hypolipidaemically effective amount of a compound as claimed in claim 1 in dosage unit form.

19. A pharmaceutical composition for the treatment or control of hypolipidaemia comprising a pharmaceutically acceptable carrier together with a hypolipidaemically effective amount of a compound as claimed in claim 1 in oral dosage unit form.

20. A pharmaceutical composition according to claim 17 in tablet, capsule, powder, granule or lozenge form or in liquid form as a sterile parenteral solution or suspension.